US008629979B2

(12) United States Patent
Tanaka

(10) Patent No.: US 8,629,979 B2
(45) Date of Patent: Jan. 14, 2014

(54) INSPECTION SYSTEM, INSPECTION METHOD, AND PROGRAM

(75) Inventor: Kazumasa Tanaka, Hitachinaka (JP)

(73) Assignee: Hitachi High-Technologies Corporation, Tokyo (JP)

( * ) Notice: Subject to any disclaimer, the term of this patent is extended or adjusted under 35 U.S.C. 154(b) by 0 days.

(21) Appl. No.: 13/817,545

(22) PCT Filed: Aug. 1, 2011

(86) PCT No.: PCT/JP2011/067598
§ 371 (c)(1), (2), (4) Date: Feb. 19, 2013

(87) PCT Pub. No.: WO2012/043058
PCT Pub. Date: Apr. 5, 2012

(65) Prior Publication Data

US 2013/0148116 A1 Jun. 13, 2013

(30) Foreign Application Priority Data

Sep. 28, 2010 (JP) ................................ 2010-217786

(51) Int. Cl.
*G01N 21/00* (2006.01)

(52) U.S. Cl.
USPC .................................... 356/237.5; 356/237.4

(58) Field of Classification Search
None
See application file for complete search history.

(56) References Cited

U.S. PATENT DOCUMENTS

2004/0160599 A1 8/2004 Hamamatsu et al.
2004/0188643 A1 9/2004 Weiss et al.
2008/0144023 A1 6/2008 Shibata et al.
2011/0149275 A1* 6/2011 Nakano et al. ............. 356/237.2
2012/0133927 A1* 5/2012 Hamamatsu et al. ...... 356/237.2
2012/0147364 A1* 6/2012 Gunji et al. ................ 356/237.2

FOREIGN PATENT DOCUMENTS

| | | | |
|---|---|---|---|
| JP | 02-174243 | A | 7/1990 |
| JP | 04-074916 | A | 3/1992 |
| JP | 2004-184142 | A | 7/2004 |
| JP | 2004-286741 | A | 10/2004 |
| JP | 2008-116405 | A | 5/2008 |
| JP | 2008-145399 | A | 6/2008 |
| JP | 2011-27485 | A | 2/2011 |
| JP | 2011-053186 | A | 3/2011 |
| JP | 2011-112449 | A | 6/2011 |
| WO | 2011/010425 | A1 | 1/2011 |

OTHER PUBLICATIONS

JP Office Action in JP App. No. 2010-217786, dated Apr. 2, 2013.

* cited by examiner

*Primary Examiner* — Gordon J Stock, Jr.
(74) *Attorney, Agent, or Firm* — Mattingly & Malur, PC

(57) ABSTRACT

Setting a spatial filter requires repeatedly confirming a scan image through visual inspection by an operator and adjusting the spatial filter. A setting state is also dependent on the operator. Therefore, in the present invention, a scattered light image (beam image) and a diffracted light image (Fourier image) are simultaneously observed, and an intensity profile of the scattered light image (beam image) and an intensity profile of the diffracted light image (Fourier image) are simultaneously monitored. A field of view of a diffracted light image is scanned with only one spatial filter, and a state change with respect to the intensity profiles in the absence of insertion of the spatial filter is detected. A setting condition for a spatial filter is determined on the basis of the detected state change.

6 Claims, 12 Drawing Sheets

1005c
1003
1012
1005b
1005a
Scan area
1003
1012
1005

1005g
1003
1005f
1012b
1012a
1005e
1005d
1051
1010_down
&
1012a_down
→
Sense amplifier
portion
1020
1000
1010
1014
1002
1001

INSPECTION SYSTEM, INSPECTION METHOD, AND PROGRAM

TECHNICAL FIELD

The present invention relates to an inspection system and an inspection method, particularly to an inspection system, an inspection method, and a program for detecting foreign matter, scratches, a defect, dirt and the like on the surface of an item to be inspected, such as a semiconductor wafer.

BACKGROUND ART

Patent Document 1 discloses an apparatus and method for detecting a defect and the like on the surface of an item to be inspected, such as a semiconductor wafer. It is described in the document that (1) an inspection recipe needs to be prepared by appropriately selecting optical conditions for a dark field of view detection optical system, such as the light-blocking shape of a spatial filter and the setting condition for a polarizing element, depending on the structure of the wafer, the pattern shape, the type of defect to be detected and the like; and (2) the selection of the optical conditions by the recipe creater can be facilitated by observing a Fourier transform plane image and a wafer image simultaneously in real-time.

Patent Document 1: Japanese Unexamined Patent Publication No. 2008-116405

SUMMARY OF THE INVENTION

Problems to be Solved by the Invention

However, according to the technique of Patent Document 1, whether the spatial filter is blocking the diffracted light associated with a specific repetition pattern formed on the wafer cannot be determined until after the scan image is confirmed. Thus, in order to optimize the spatial filter setting, it has been necessary to repeatedly confirm the scan image. Further, in the case of Patent Document 1, the problem that the setting conditions regarding the width and interval (pitch) of the spatial filter depend on the operator is not considered.

Solutions to the Problems

The present inventor conducted detailed analysis of the problems and invented a mechanism by which a spatial filter suitable for inspecting an item to be inspected can be automatically set in a short time. According to the present invention, by using a processor, both an intensity profile of a scattered light image (beam image) and an intensity profile of a diffracted light image (Fourier image) of the item to be inspected are simultaneously observed, and the setting conditions for a spatial filter for selectively blocking the diffracted light due to a specific pattern on the surface of the item to be inspected are determined on the basis of the result of observation.

Effects of the Invention

According to the present invention, the setting condition for the spatial filter for selectively blocking only the diffracted light due to a specific pattern on the surface of an item to be inspected can be automatically determined. Further, a spatial filter setting that is not operator-dependent can be implemented.

MODE FOR CARRYING OUT THE INVENTION

In the following, embodiments of the present invention will be described with reference to the drawings. The present invention is not limited to the following embodiments, and various modifications of the embodiments may be made within the technical scope of the present invention.

First Embodiment

Figure 1:
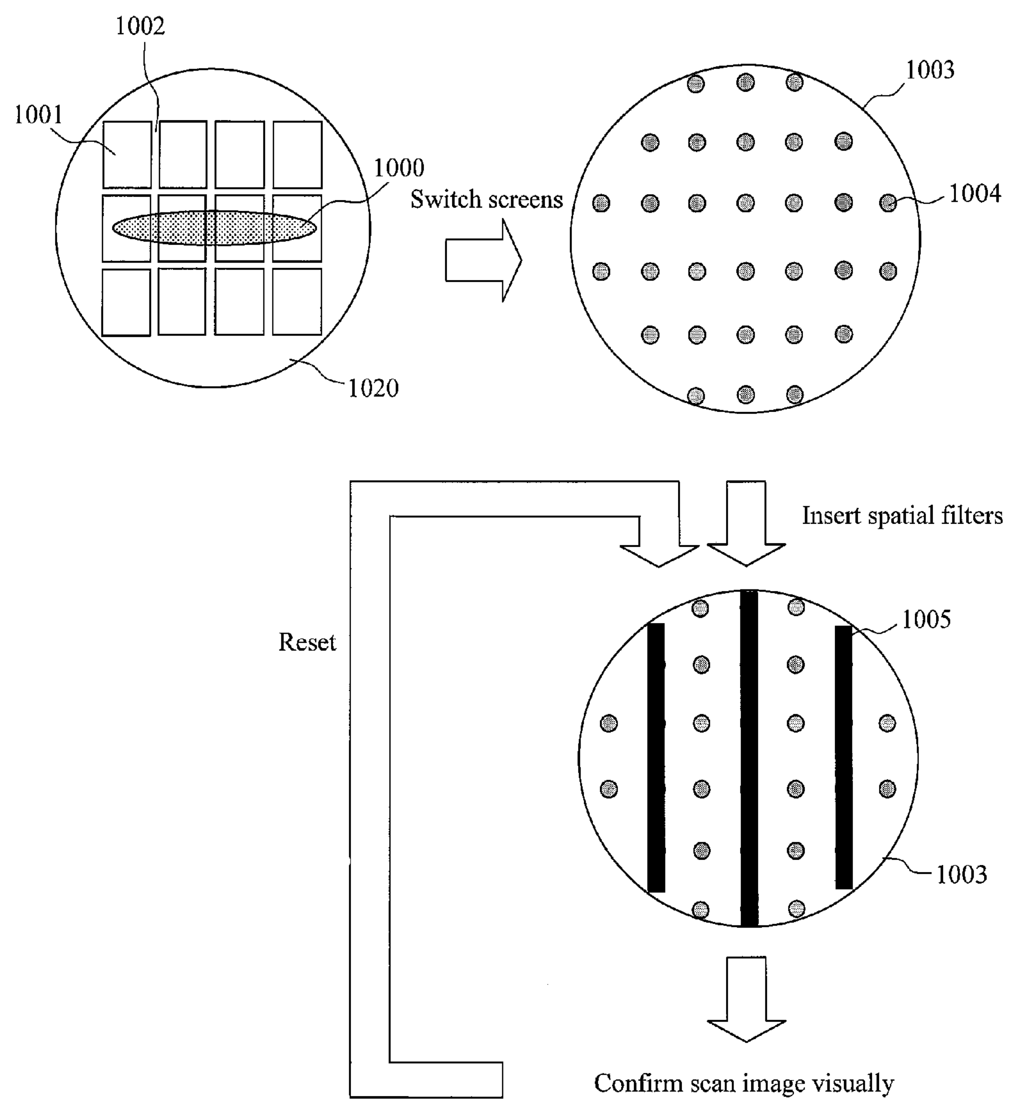
FIG. 1 illustrates a spatial filter setting method according to related art.

FIG. 1 illustrates a spatial filter setting method according to related art. First, an inspection stage is moved such that an irradiation beam 1000 with which a surface of a wafer is irradiated can irradiate a chip to be inspected. The irradiation beam 1000 is irradiated across a plurality of cell portions 1001 and a plurality of sense amplifier (S/A) portions 1002 that are formed on the wafer as a repetition pattern. The numeral 1020 designates a beam image acquired by scanning the irradiation beam 1000.

As the wafer surface is irradiated with the beam 1000, diffracted light 1004 corresponding to the cell portions 1001 and the sense amplifier portions 1002 appears in a Fourier image 1003 as dot images. The dot image has periodicity. In order to observe a defect in an area of the cell portions 1001 or the sense amplifier portions 1002, it is necessary to set a spatial filter at an optimum position such that only the diffracted light component due to the cell portions 1001 or the sense amplifier portions 1002 can be blocked. By blocking only the periodic diffracted light component, only the non-periodic diffracted light component due to the defect can be selectively observed.

As the spatial filter is inserted, an image 1005 of the spatial filter is observed in the Fourier image 1003. However, the determination as to whether the spatial filter is blocking the diffracted light arising from an intended area needs to be made by re-acquiring the scan image of the wafer surface with the spatial filter set, and confirming the result by visual inspection by the operator. When the re-acquired scan image differs from what was intended, it is necessary to repeat the resetting of the spatial filter, re-acquiring of the wafer surface scan image, and the confirming of the result by visual inspection.

In contrast, according to a spatial filter setting method described in the present specification, both an intensity profile of the beam image and an intensity profile of the Fourier image are simultaneously observed by a processor, and the spatial filter is automatically set on the basis of the observation result.

Figure 2:
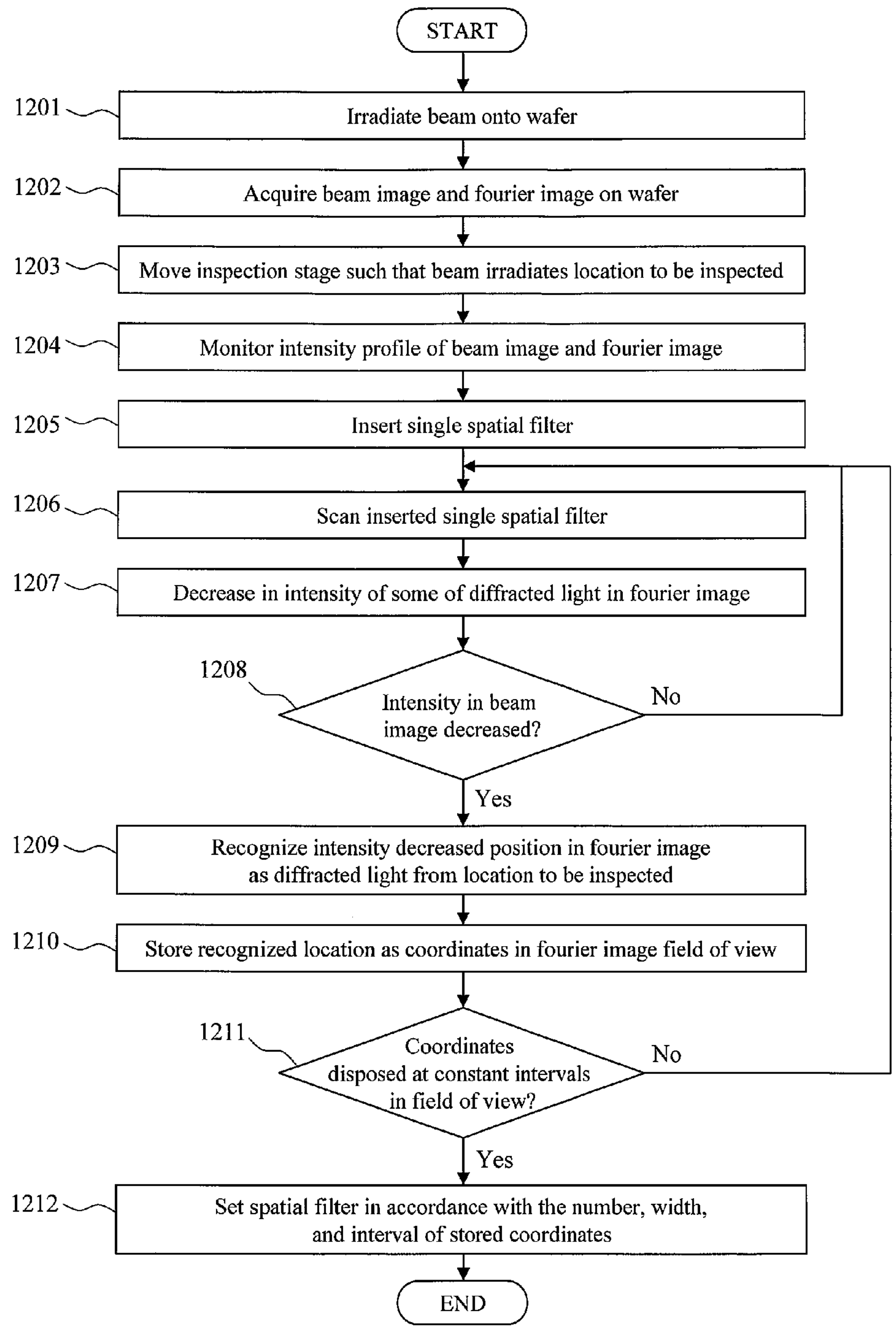
FIG. 2 is a flowchart illustrating a spatial filter setting procedure according to an embodiment.

In the following, a spatial filter setting procedure according to an embodiment will be described with reference to the flowchart of FIG. 2. The flowchart of FIG. 2 may be implemented not only by a processor dedicated for the spatial filter setting process but also by another cooperating processor.

Figure 3:
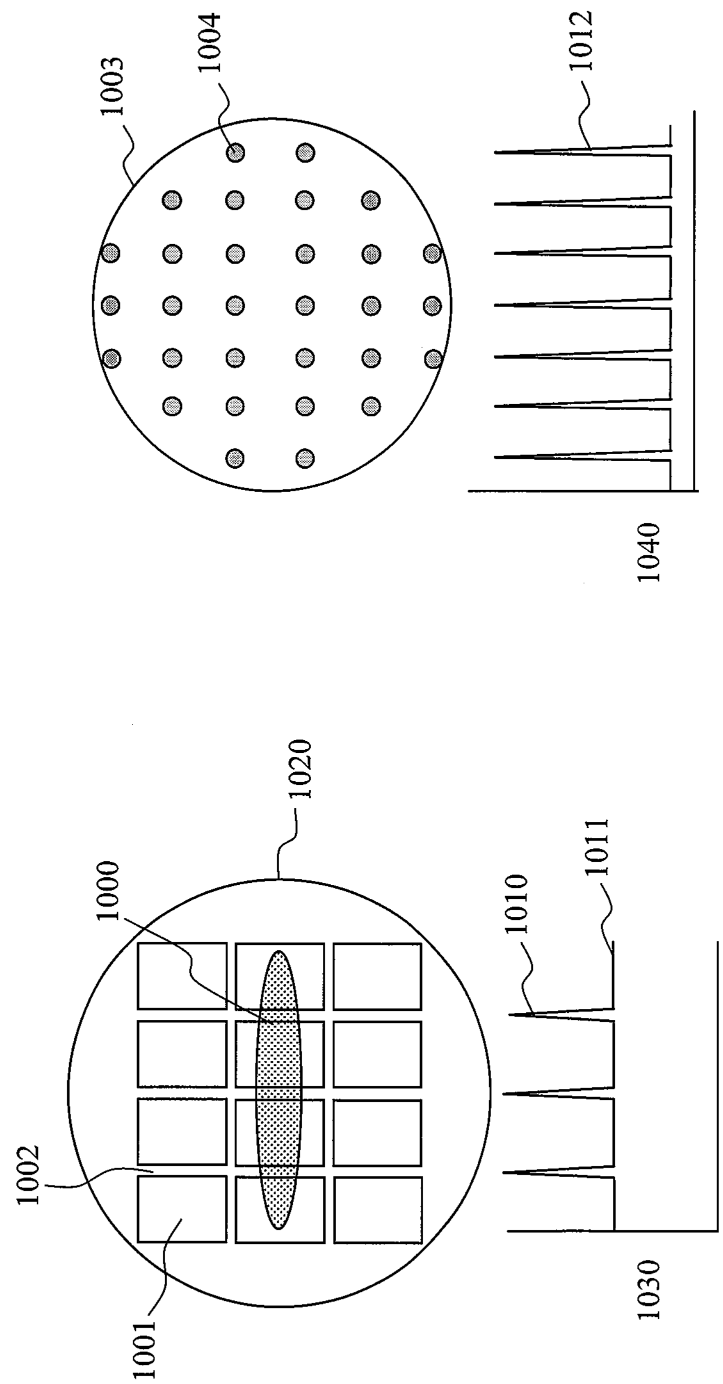
FIG. 3 illustrates examples of intensity profiles observed prior to insertion of a spatial filter.

According to the present embodiment, as illustrated in FIG. 3, the setting conditions for the spatial filter is determined by using not only the beam image 1020 and the Fourier image 1003 but also intensity profiles 1030 and 1040 thereof simultaneously. More specifically, both the intensity profile 1030 of the beam image 1020 and the intensity profile 1040 of the Fourier image 1003 are simultaneously observed by the processor, and the number, width, interval (pitch), and arrangement of the spatial filters are determined in accordance with the observation result.

In the case of the intensity profile 1030 corresponding to the beam image 1020, an intensity profile 1011 corresponding to the cell portions 1001 shines by a base (reference) strength, while an intensity profile 1010 corresponding to the sense amplifier portions 1002 has a pattern arrangement that appears in a pulsed manner with respect to the base strength.

Meanwhile, in the case of the intensity profile 1040 corresponding to the Fourier image 1003, portions other than the dot images shines by a base (reference) strength, while an intensity profile 1012 corresponding to the dot images 1004 has a pattern arrangement that appears in a pulse manner with respect to the base strength.

According to the present embodiment, by focusing on a state change in the intensity profiles, the process of setting the spatial filter for blocking only the diffracted light from the cell portions 1001 or the sense amplifier portions 1002 is automated.

First, in step 1201, the processor causes the irradiation beam 1000 to irradiate the wafer. In the next step 1202, the processor acquires both the beam image 1020 and the Fourier image 1003 on the wafer from imaging cameras. At this point, in the Fourier image 1003, the diffracted light corresponding to the cell portions 1001 and the sense amplifier portions 1002, i.e., the repetition patterns, appears as the periodic dot images 1004.

In step 1203, the processor causes the inspection stage to be moved such that the beam 1000 irradiates a location to be inspected. At this point, the beam 1000 irradiates across the cell portions 1001 and the sense amplifier portions 1002 in the chip. The sense amplifier portions 1002 refer to a peripheral circuit pattern for writing and reading data to or from the cell portions 1001.

In step 1204, the processor generates the intensity profiles from the beam image 1020 and the Fourier image 1003 acquired from the location to be inspected, and sets the intensity profiles as objects for monitoring. At this point, the intensity profile 1030 of the beam image and the intensity profile 1040 of the Fourier image are stored in a storage area for detecting a state change. The intensity profiles 1030 and 1040 that are stored herein represent information for the case in which no spatial filter is inserted.

In step 1205, the processor causes a single spatial filter to be inserted in the Fourier plane (focal plane of a image-forming lens) so that a change in the intensity profiles in accordance with the scan position of the spatial filter can be observed, as will be described later.

Figure 4:
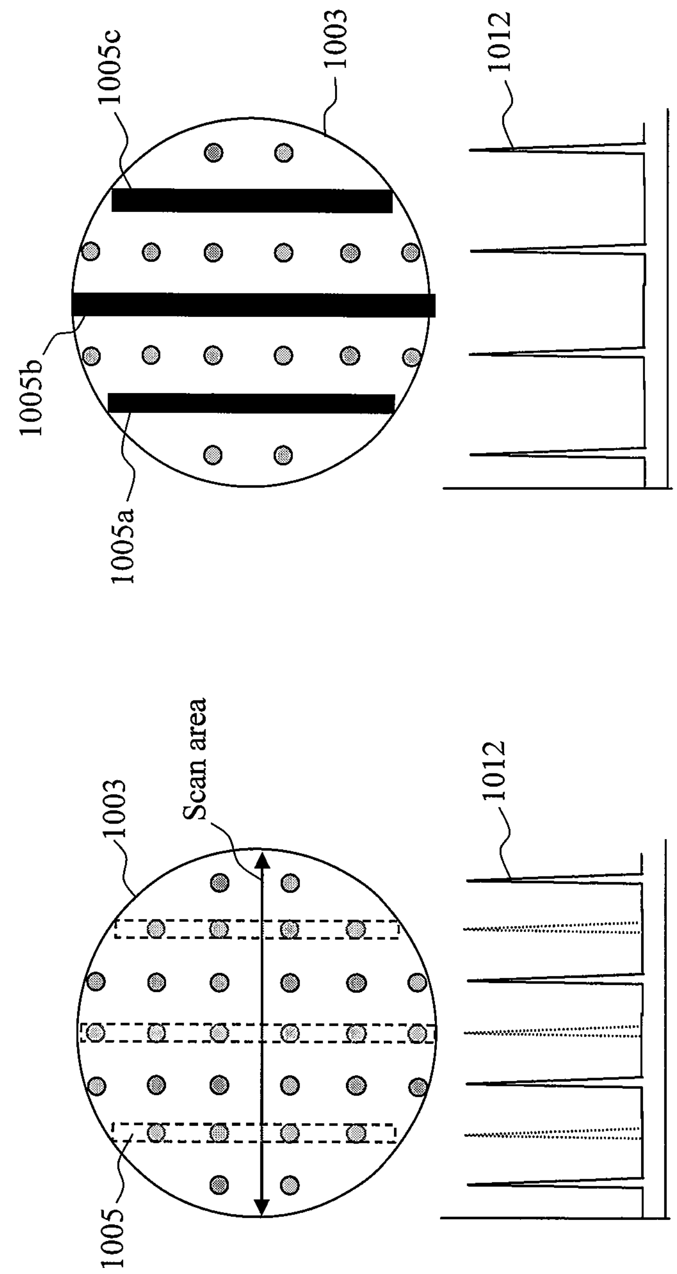
FIG. 4 illustrates a state change in intensity profile observed in the spatial filter setting process and an intensity profile after the setting.

In step 1206, the processor scans the field of view of the Fourier image from end to end with the inserted single spatial filter, as indicated by an arrow in FIG. 4. The intensity profile 1012 on the left in FIG. 4 indicates that there is a decrease in intensity profile when the spatial filter completely hides the diffracted light from the sense amplifier portions 1002, as indicated by the broken lines. The right-hand side of FIG. 4 illustrates an example of a spatial filter arrangement in which the number, width, and interval of the special filters are optimized. The example illustrates the Fourier image 1003 and the intensity profile 1012 thereof after three spatial filters 1005*a* to 1005*c* are disposed at predetermined positions.

Figure 5:
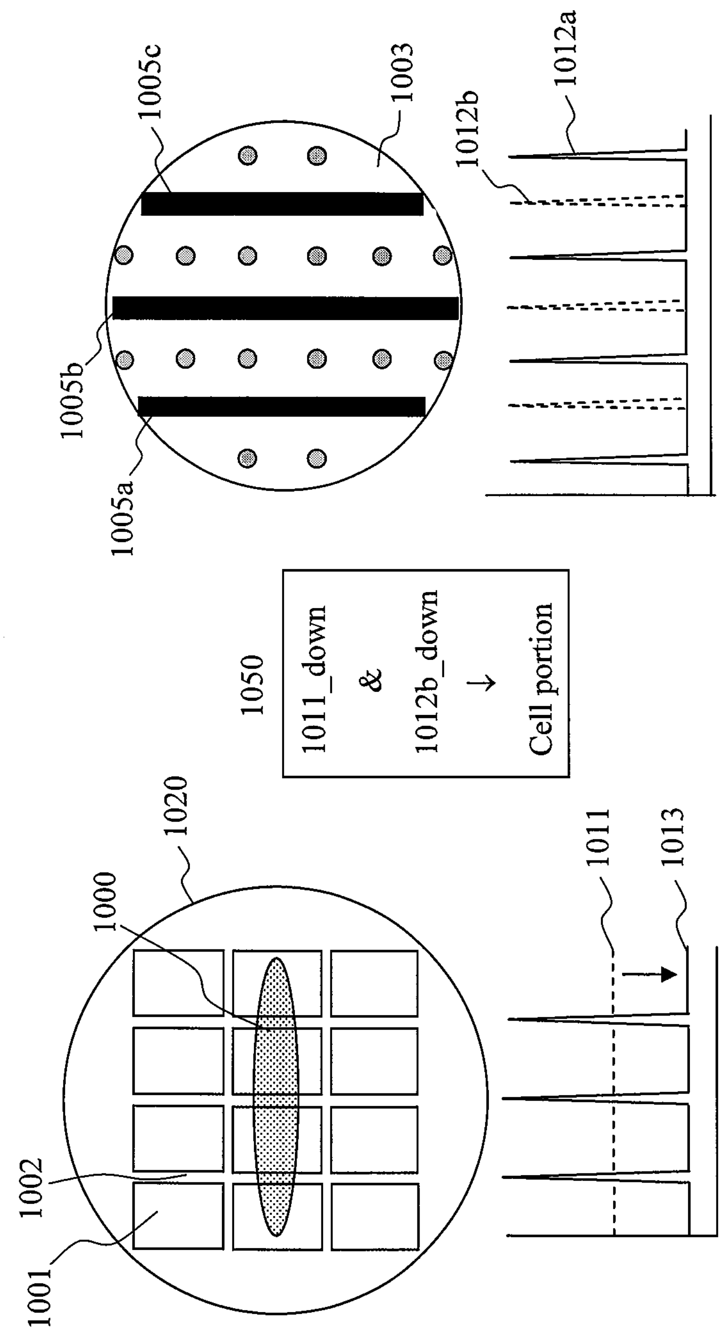
FIG. 5 illustrates a state change in intensity profile that appears when the spatial filter blocks the diffracted light from a cell portion.
Figure 6:
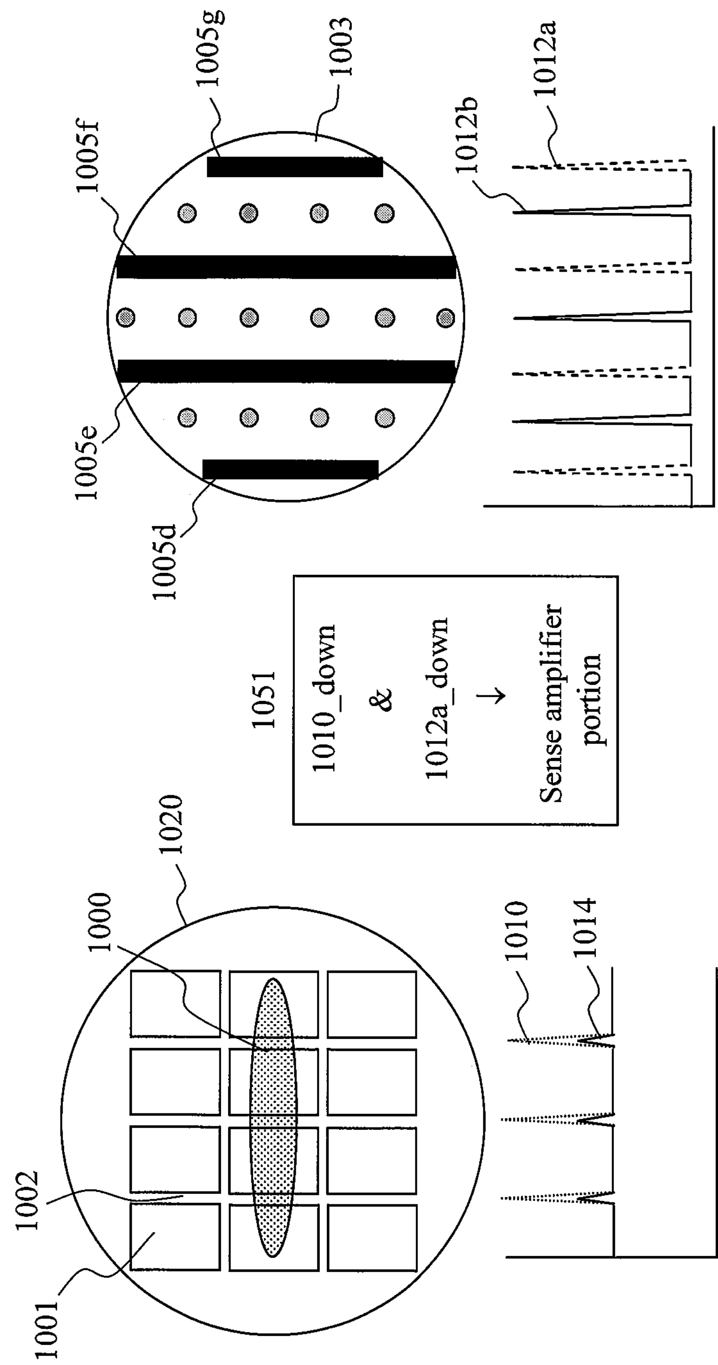
FIG. 6 illustrates a state change in intensity profile that appears when the spatial filter blocks the diffracted light from a sense amplifier portion.

Steps 1207 to 1210 specify operations of the processor that are performed in response to a state change in the intensity profile 1030 of the beam image and the intensity profile 1040 of the Fourier image that appears as the spatial filter is moved within the scan area. FIGS. 5 and 6 illustrate combinations of the state changes in the intensity profiles as the objects for monitoring by the processor.

In step 1207, the processor confirms a decrease in one of the pulsed intensity patterns of the intensity profile of the Fourier image. The decrease is confirmed by comparison with the intensity profile acquired in step 1204.

In step 1208, the processor determines whether a decrease is observed in the intensity profile of the beam image. When a negative result is obtained, the processor determines that there is no decrease in the periodic intensity profile which is the object for monitoring, returns to step 1206, and continues the spatial filter scan. When an affirmative result is obtained, the processor proceeds to the next step 1209.

In step 1209, the processor recognizes the position at which the decrease in intensity profile is observed as diffracted light from the periodic area as the object of inspection. As illustrated in FIG. 5, when a decrease in the intensity profile 1011 shining by the base strength in the intensity profile of the beam image 1020 is detected and when a decrease in the pulsed intensity profiles 1012*b* in the intensity profile of the Fourier image 1003 is detected; namely, when recognition conditions 1050 are satisfied, the processor recognizes a position at which the diffracted light from the cell portions 1001 is blocked. When the beam image 1020 can be observed by the operator, the state in which the recognition conditions 1050 are satisfied may be also visually recognized by noting an overall darkening of the repetition pattern image in the beam image 1020 being observed.

When, as illustrated in FIG. 6, a decrease in intensity is detected in the pulsed profile 1010 in the intensity profile of the beam image 1020 and when a decrease in intensity is detected in one of the pulsed profiles 1012*a* in the intensity profile of the Fourier image 1003; namely, when conditions 1051 are satisfied, the processor recognizes a position at which the diffracted light from the sense amplifier portions 1002 is blocked.

In step 1210, the processor stores the recognized positions in the storage area as coordinate values within the field of view of the Fourier image. At this point, information identifying the spatial filter that produced the decrease in the intensity profile of the beam image 1020 and the decrease in the intensity profile of the Fourier image 1003 is also stored in association with the position information.

In step 1211, the processor determines whether the coordinates stored as the positions satisfying the recognition conditions 1050 or 1051 have a certain interval in the field of view of the Fourier image 1003. When a negative result is obtained, the processor determines that the detection result contains non-periodic information, returns to step 1206, and repeats the scan operation and the coordinate position detection operation by changing the scan speed or width of the spatial filter. When an affirmative result is obtained, the processor proceeds to step 1212.

In step 1212, the processor sets the number, width (thickness), interval (distance between the spatial filters), and coordinate positions of the spatial filters such that the spatial filters are arranged at all of the coordinate positions stored in the recognition conditions 1050 (for the cell portions) or the recognition conditions 1051 (for the sense amplifier portions). These setting conditions (the number, width, interval, and coordinate positions of the spatial filters) are stored in the storage area. Thereafter, the spatial filter setting process by the processor ends.

When the cell portions 1001 are inspected for a defect and the like, the processor reads the setting conditions for inspection of the cell portions 1001 from the storage area, and causes the spatial filters to be disposed at predetermined positions in a detection optical system. In the Fourier image 1003 illustrated in the right-hand side of FIG. 5, the three spatial filters 1005*a*, 1005*b*, and 1005*c* (blackened-out portions) are set for observing a defect in the cell portions 1001. In this case, from the intensity profile of the Fourier image, three pulsed intensity profiles 1012*b* indicated by broken lines are eliminated. With regard to the beam image, as illustrated in the left-hand side of FIG. 5, the intensity (level) of the intensity profile 1011 is decreased to the intensity (level) of the intensity profile 1013. Thus, a defect and the like that may be hidden in the intensity profile 1011 can be confirmed within the beam image 1020.

Meanwhile, when the sense amplifier portions 1002 are inspected for a defect and the like, the processor reads the setting conditions for inspection of the sense amplifier portions 1002 from the storage area, and causes the spatial filters to be disposed at predetermined positions in the detection optical system. In the Fourier image 1003 illustrated in the right-hand side of FIG. 6, four spatial filters 1005*d*, 1005*e*, 1005*f*, and 1005*g* (blackened-out portions) are set for defect observation of the sense amplifier portions 1002. In this case, four pulsed intensity profiles 1012*a* indicated by broken lines are eliminated from the intensity profile of the Fourier image. With regard to the beam image, as illustrated in the left-hand side of FIG. 6, the intensity (level) of the pulsed intensity profile 1010 corresponding to the sense amplifier portions 1002 is decreased to the intensity (level) of intensity profiles 1014. Thus, a defect and the like that may be hidden in the intensity profile 1010 can be confirmed in the beam image 1020.

As described above, according to the present embodiment, the setting conditions for the spatial filters (number, width, interval, and coordinate position) for blocking only the diffracted light from a periodic pattern that appears in the wafer can be determined simply through data processing by the processor. Namely, a spatial filter arrangement optimized for detecting a non-uniform (non-periodic) diffracted light component of the diffracted light from the wafer can be automatically set.

Thus, the technique according to the present embodiment does not involve a decision by the individual operator when setting the spatial filters. Accordingly, the possibility of individual differences in the setting of the spatial filters according to a related-art technique can be eliminated. In other words, the variation in the inspection result obtained by an inspection apparatus using spatial filters can be eliminated.

Further, by the technique according to the present embodiment, an optimized spatial filter arrangement can be uniquely determined through detection of a state change in the intensity profile of each of the beam image and the Fourier image. Thus, the need for repeatedly adjusting the spatial filters, acquiring the beam image, and confirming the appropriateness of adjusted positions by visual inspection before the spatial filter setting is finalized, as required by a related-art technique, can be eliminated. In this way, the time required for determining the optimized filter arrangement can be greatly decreased.

Second Embodiment

According to the first embodiment, the processor to which the image data of the beam image and the Fourier image are inputted generates the corresponding intensity profiles and, based on a combination of the state changes in the two intensity profiles, automatically determines the setting conditions for the spatial filters suitable for detecting a defect and the like in the cell portions and the setting conditions for the spatial filters suitable for detecting a defect and the like in the sense amplifier portions. Namely, the first embodiment does not assume that the beam image, the Fourier image, the intensity profile of the beam image, and the intensity profile of the Fourier image are presented to the operator.

However, the beam image, the Fourier image, the intensity profile of the beam image, and the intensity profile of the Fourier image may be displayed on an operating screen and the like in real-time in parallel with the automatic setting operation for the spatial filter by the processor. Whether such display should be provided or not may be selected by the operator. When such a display function is provided, the operator can confirm on-screen whether the spatial filter setting automatically set on the inspection system side is appropriate. For example, the operator can confirm the effect of the automatically set spatial filters in blocking the diffracted light from the cell portions 1001 by visually observing a decrease in brightness of the beam image as a whole or a decrease in the intensity profile thereof.

Third Embodiment

Next, an example of a spatial filter drive mechanism will be described. By using the technique described with reference to the first embodiment, the number, width, interval (pitch), and coordinate positions of the spatial filters that are optimized for blocking the diffracted light can be automatically set. However, in order for the setting to be effective, spatial filters of which the number, width, interval, and coordinate positions can be freely set are required.

Figure 7:
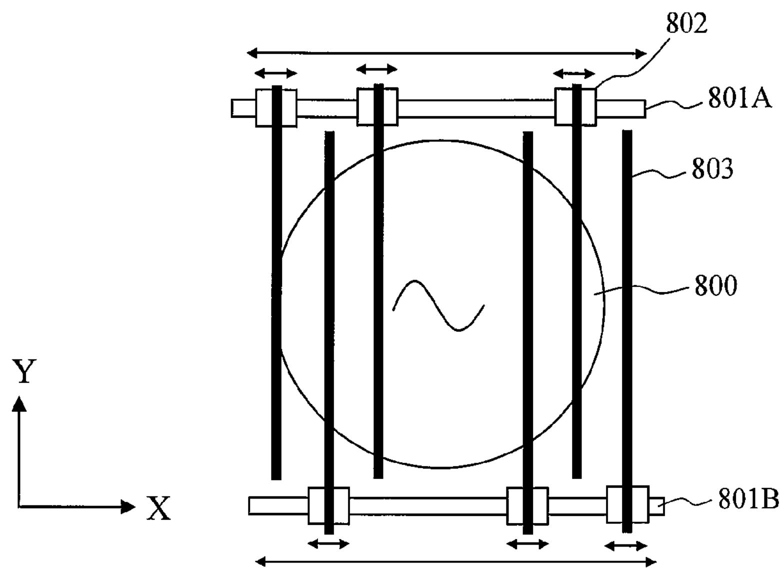
FIG. 7 illustrates an arrangement/structure of spatial filters using ultrasonic motors.
Figure 8:
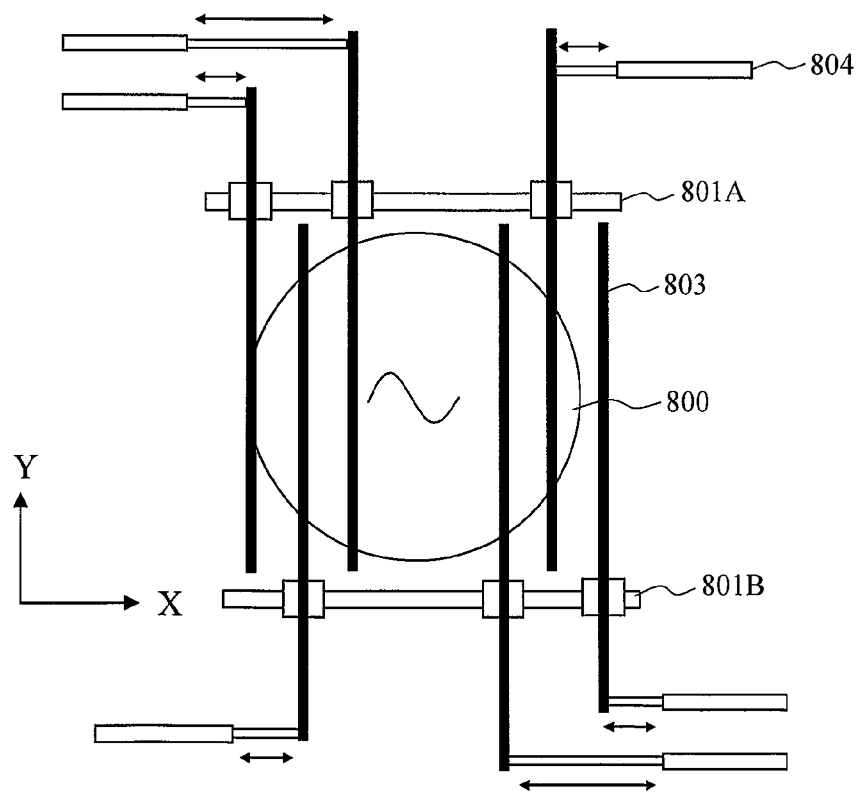
FIG. 8 illustrates an arrangement/structure of spatial filters using small-sized linear encoders.

FIGS. 7 and 8 illustrate configurations of this type of spatial filter. In FIGS. 7 and 8, two sets of three spatial filters are disposed by way of example. The six spatial filters have the same, fixed width.

In this case, when the width of the spatial filters need not be varied, the two sets of spatial filters may be all disposed on the image surface of pupil of the Fourier image 1003. When it is necessary to vary the width of the spatial filters, the two sets of spatial filters may be disposed on both sides of the image surface of pupil of the Fourier image 1003 with a predetermined distance of offset. In this case, the two sets of spatial filters are moved on different movement planes. Thus, the spatial filter arrangements of the respective sets can be overlapped such that the width of the spatial filters can be increased by up to two times. Such a combination of the two spatial filters arranged at different levels will also be handled as a single spatial filter from the viewpoint of light-blocking effect.

In the examples of FIGS. 7 and 8, the spatial filters 803 are positioned along two slide rails 801A and 801B extending in an X-axis direction. The two slide rails 801A and 801B may be disposed on the same plane as the image surface of pupil 800, or at height positions across the image surface of pupil 800 that are offset in an optical axis direction such that the inspection light flux can be avoided.

The spatial filters 803 have a long and thin rectangular shape in the XY plane. Parts of the spatial filters 803 are movably attached to the slide rails 801A and 801B via attaching members. In the example of FIG. 7, ultrasonic motors 802 are attached to the attaching members so that the attaching members themselves can be linearly driven by the ultrasonic motors 802. In the example of FIG. 8, no self-propelled mechanism is attached to the attaching members; instead, one end of the spatial filters 803 is attached to a movable axle of linear encoders 804. Thus, in the case of FIG. 8, the position of the spatial filters 803 in the X-axis direction can be determined by varying the axial length of the linear encoders 804.

As indicated by arrows in FIGS. 7 and 8, the spatial filters 803 can be positioned mutually independently. Because the individual spatial filters 803 can be freely positioned, the number, width, interval, and position of the spatial filters 803 used for blocking the diffracted light can be freely set.

Figure 9:
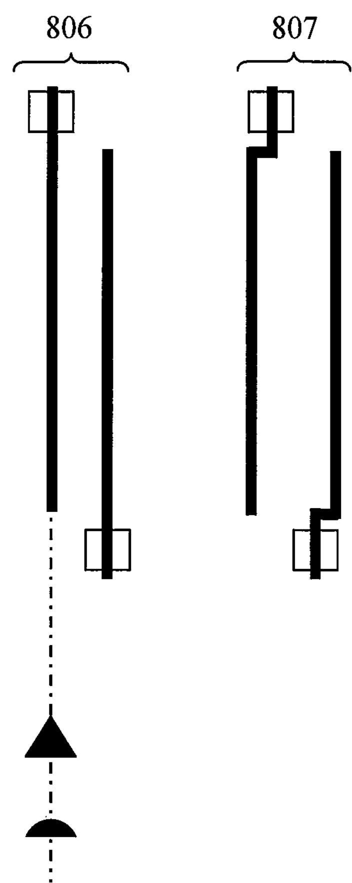
FIG. 9 illustrates examples of cross-sectional shape of the spatial filters.

While in FIGS. 7 and 8 the spatial filters 803 have the long and thin rectangular shape in the XY plane, it may be preferable to provide a mechanism by which the shape of the spatial filters 803 can be freely switched to a straight bar shape or a key shape in accordance with the shape of the diffracted light from the repetition pattern. FIG. 9 illustrates spatial filters 806 of the straight bar shape and spatial filters 807 of the key shape. The spatial filters may have a triangular or semicircular cross-sectional shape.

The spatial filters may be formed in a lattice in the XY plane, and a mechanism for blocking lattice-shaped diffracted light from a repetition pattern on the wafer may be provided.

Fourth Embodiment

In the following, a configuration of an inspection system provided with the spatial filter automatic setting function and the spatial filter drive mechanism described above will be described.

(System Configuration)

Figure 10:
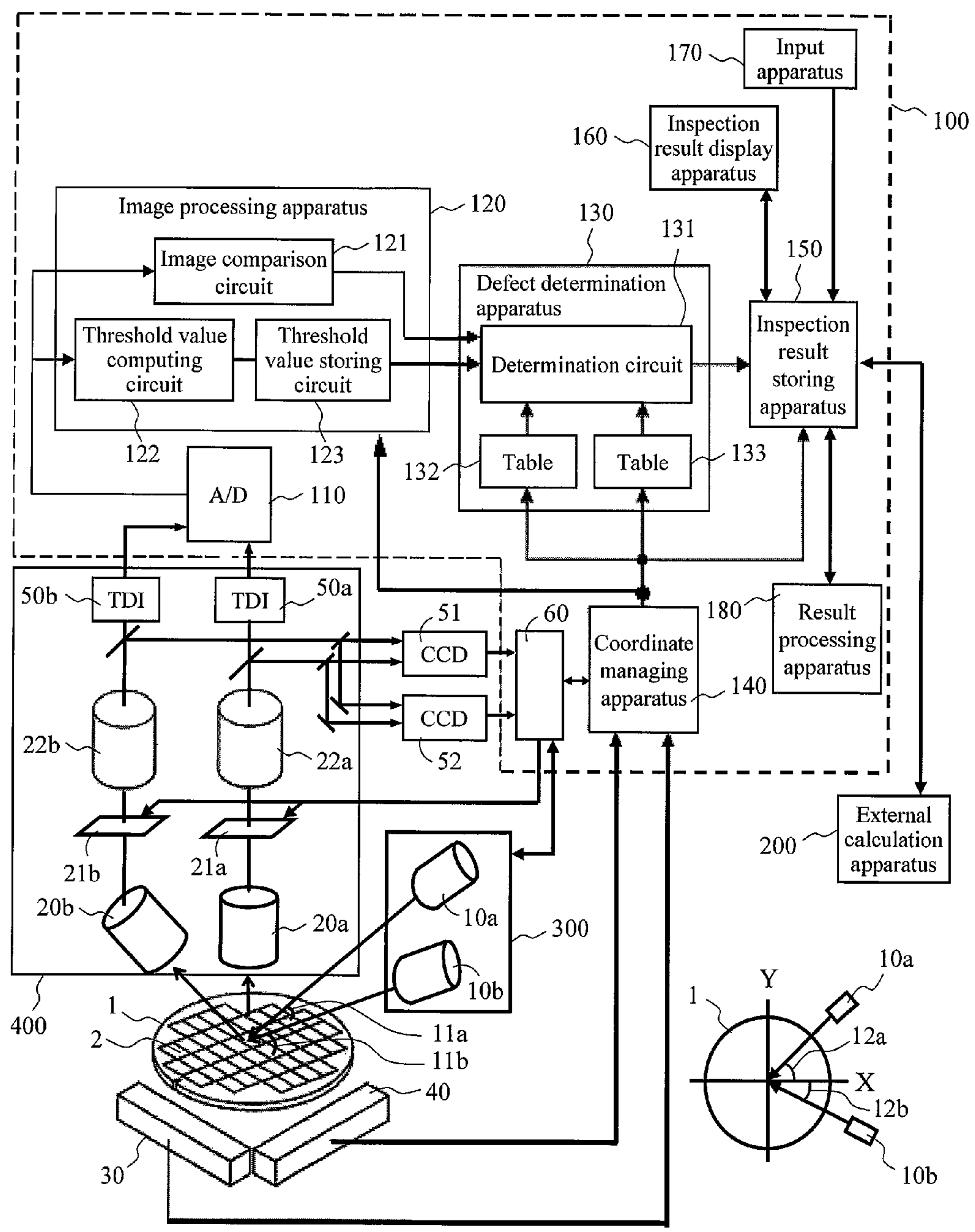
FIG. 10 schematically illustrates a configuration of an inspection system according to an embodiment.

FIG. 10 schematically illustrates a configuration of the inspection system according to the present embodiment. The inspection system illustrated in FIG. 10 includes an illumination unit 300; a detection unit 400; an X-scale 30; a Y-scale 40; and a processing apparatus 100. The inspection system may also include an external calculation apparatus 200 as needed. The inspection system according to the present embodiment is an optical inspection system that uses a dark-field image.

The illumination unit 300 may include a laser apparatus that produces inspection light, such as laser light, with a predetermined wavelength. The produced inspection light is used for irradiating the surface of a wafer 1 as an item to be inspected. According to the present embodiment, the inspection light is produced by each of illumination light sources 10*a* and 10*b*.

On the surface of the wafer 1, the chips 2 are formed in a matrix. The wafer 1 is mounted on an XY stage 70 (FIG. 11) so that the wafer 1 can be moved in XY-directions by the XY stage. As the wafer 1 is moved in the X-direction or the Y-direction, the inspection light moves in such a manner as to scan the surface of the wafer 1.

The illumination light sources 10*a* and 10*b* irradiate the surface of the wafer 1 from diagonally above at angles determined by elevation angles 11*a* and 11*b*, respectively. While not illustrated, a mechanism is provided for changing the elevation angles 11*a* and 11*b* as desired. The illumination light sources 10*a* and 10*b* are also provided with a mechanism for switching the polarization of illumination light as desired depending on the type of the item to be inspected or the size of the defect to be detected. Further, the illumination light sources 10*a* and 10*b* are provided with an automatic adjustment mechanism such that a predetermined location of the surface of the wafer 1 as the item to be inspected can be irradiated with inspection light at all times.

Figure 11:
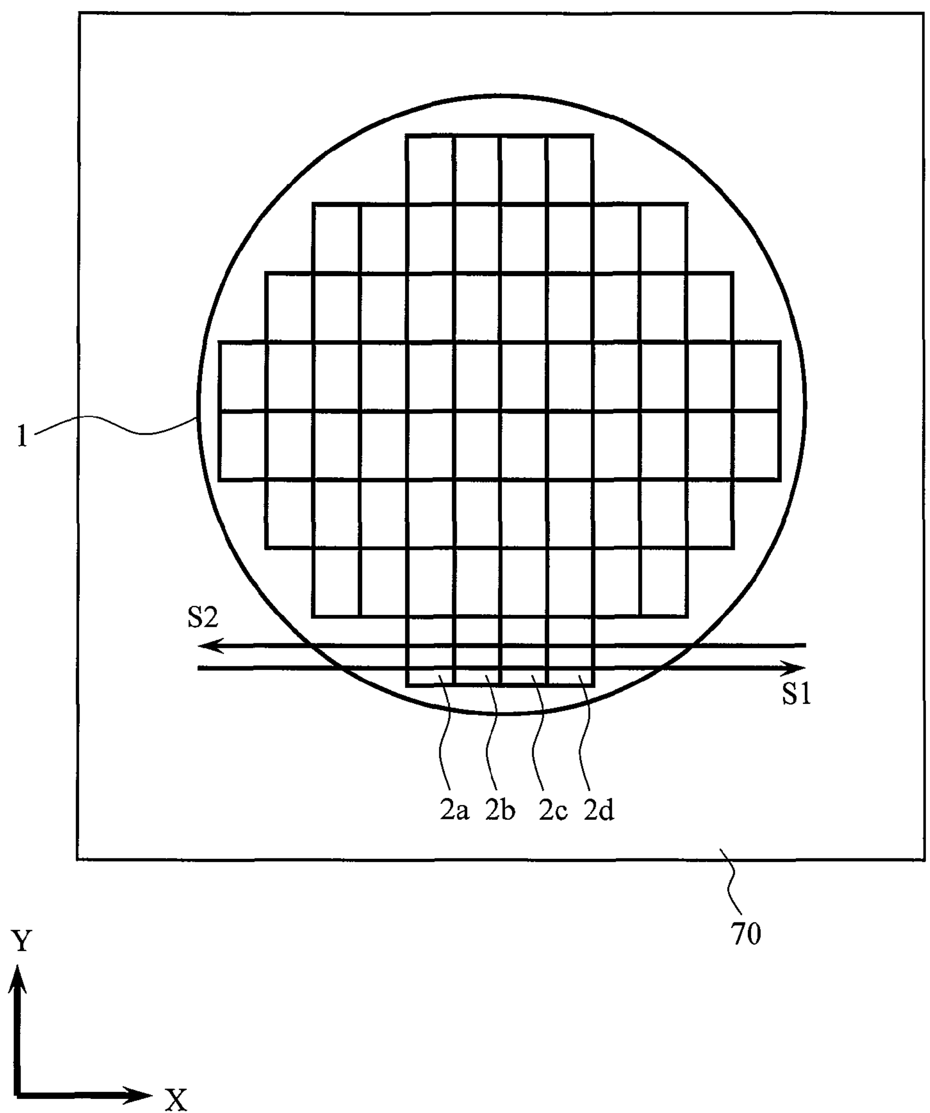
FIG. 11 illustrates inspection light scan directions.

With reference to FIG. 11, scanning of the wafer surface with inspection light will be described. When the XY stage 70 with the wafer 1 mounted thereon is moved in a -X-direction, the inspection light is moved in an X-direction indicated by an arrow S1. Namely, the inspection light illuminates the chips formed on the wafer 1 in the order of 2*a*, 2*b*, 2*c*, and 2*d*. In this way, a first line of scan in the X-direction is performed. Then, the XY stage 70 is moved in a -Y-direction, whereby the line to be scanned by the inspection light is shifted in a Y-direction. Thereafter, as the XY stage 70 is moved in the X-direction, the inspection light is moved in the -X-direction indicated by an arrow S2. Namely, the inspection light illuminates the chips formed on the wafer 1 in the order of 2*d*, 2*c*, 2*b*, and 2*a*. In this way, a second line of scan in the X-direction is performed. By repeating these operations, the entire surface of the wafer 1 is scanned by the inspection light. The XY stage is provided with a mechanism for setting the moving speed of the XY stage in the respective directions as desired in accordance with predetermined conditions, such as the type of the item to be inspected or the size of the defect to be detected.

Referring back to FIG. 10, the inspection light with which the surface of the wafer 1 is irradiated is scattered by a pattern or a defect on the surface of the wafer 1, producing scattered light. The detection unit 400, which may include a condensing lens, a TDI (Time Delay Integration) sensor and the like, receives the scattered light produced at the surface of the wafer 1 with a detector 50*a* (TDI sensor according to the present embodiment) and converts the intensity of the scattered light into an electric signal. The electric signal after the conversion is outputted to the processing apparatus 100 as an image signal. The detector 50*a* (50*b*) may include a CCD sensor.

The TDI sensor has N pixels×M lines. Because of this structure, the TDI sensor can perform shifting and successive summing of charges in the line direction repeatedly, so that M times of charge can be accumulated. Based on this feature, the charge shift speed in the line direction and the moving speed of the item to be inspected can be made the same, whereby a highly sensitive and low-noise image can be acquired. The maximum charge shifting speed of the TDI sensor in the line direction may be referred to as a “line rate”.

In this type of an inspection system, when a pattern of the chips is formed on the surface of the wafer, normally an image signal is produced from the intensity of the detected scattered light, the image signal for an inspection area (an inspection chip or an inspection shot) is compared with an image signal for a reference area (a reference chip or a reference shot), and a location at which the difference between the image signals is not less than a threshold value is determined to be foreign matter. For the reference area, an area adjacent to the inspection area (an adjacent chip or an adjacent shot), or a conforming area (a conforming chip or a conforming shot) prepared in advance may be used.

The required sensitivity and the required inspection time for the inspection system, and the time for preparing a recipe may greatly vary depending on the type of wafer, the process therefor, or a client management method.

The illumination unit 300 and the detection unit 400 are a combination of a plurality of illumination means and detection means including an objective lens 20*a*, a spatial filter 21*a*, a image-forming lens 22*a*, and the detector 50*a* which are dedicated for the illumination means 10*a*; and an objective lens 20*b*, a spatial filter 21*b*, a image-forming lens 22*b*, and the detector 50*b* which are dedicated for the illumination means 10*b*.

The objective lens 20*a* is a lens for receiving and condensing the diffracted light produced at the surface of the wafer 1, and provided with an individual lens mechanism for the detector 50*a*. Similarly, the objective lens 20*b* is provided with an individual lens mechanism for the detector 50*b*.

The image-forming lens 22*a* is provided with a mechanism for switching several image-forming lenses with individual magnification ratios for changing detection sensitivity as desired depending on the type of item to be inspected or the size of the defect to be detected.

The image-forming lens 22*a* and the image-forming lens 22*b* may be provided with a single image-forming lens with switchable magnification ratios for changing detection sensitivity depending on the type of item to be inspected or the size of the defect to be detected, such as a zoom lens.

The image-forming lens 22*a* and the image-forming lens 22*b* may be provided with a image-forming lens with a plurality of detection angles which are selectable depending on the type of item to be inspected or the size of the defect to be detected.

For the spatial filters 21*a* and 21*b*, the spatial filters described with reference to FIGS. 7 to 9 are used. The spatial filters 21*a* and 21*b* are disposed on an image surface of pupil of the Fourier plane. The beam image and the Fourier image which are used for automatic setting of the spatial filters are acquired by detectors 51 and 52 to which one of the light fluxes split by beam splitters disposed on the optical axes of the image-forming lens 22*a* and 22*b* is guided. The image (beam image) for the other light flux is acquired at the imaging plane of the detectors 50*a* and 50*b*, as described above.

According to the present embodiment, the beam image for setting the spatial filters is acquired by the detector 51 (CCD sensor in the illustrated example). The Fourier image for setting the spatial filters is acquired by the detector 52 (CCD sensor in the illustrated example). On the imaging plane of the detector 52, an optical filter which is not illustrated is disposed and configured such that the Fourier image can be obtained through the optical filter. Image data obtained by the detectors 51 and 52 are fed to the spatial filter setting apparatus 60. The spatial filter setting apparatus 60 generates intensity profile data for each of the beam image and the Fourier image. As described above, the spatial filter setting apparatus 60 observes the beam image, the intensity profile thereof, the Fourier image, and the intensity profile thereof simultaneously, and determines, through the scanning of a single spatial filter, the number, width, interval, and coordinate positions of the spatial filters for blocking the diffracted light from a periodic specific pattern. The spatial filter setting apparatus 60, when the inspection area for a defect and the like is designated via the input apparatus 170 and the like, controls the arrangement of the spatial filters 21*a* and 21*b* individually in accordance with the setting conditions suitable for observing the inspection area.

The spatial filter setting apparatus 60 is connected to an inspection result display apparatus 160, so that the beam image, the intensity profile thereof, the Fourier image, and the intensity profile thereof can be displayed simultaneously on a display screen of the inspection result display apparatus 160 upon request from the operator. The spatial filter setting apparatus 60 cooperates with a control unit (not illustrated) for the illumination unit 300 and a coordinate managing apparatus 140. According to the present embodiment, the spatial filter setting unit 60 functions as a control unit for the irradiation unit 300, the detection unit 400, and the XY stage 70.

The X-scale 30 and the Y-scale 40 include a laser scale and the like, for example. The X-scale 30 and the Y-scale 40 detect an X-direction position and a Y-direction position, respectively, of the XY stage 70 with the wafer 1 mounted thereon, and output the position information to the processing apparatus 100.

The processing apparatus 100 is provided with an A/D converter 110, an image processing apparatus 120, a defect determination apparatus 130, the coordinate managing apparatus 140, an inspection result storage apparatus 150, the inspection result display apparatus 160, the input apparatus 170, and a result processing apparatus 180.

The A/D converter 110 converts an image signal of an analog signal received from the detection unit 400 including the detector 50*a* or 50*b* into a digital image signal and outputs the digital signal.

The image processing apparatus 120 is provided with an image comparison circuit 121, a threshold value computing circuit 122, and a threshold value storing circuit 123.

The image comparison circuit 121 is provided with a delay circuit and a difference detection circuit, for example. The image comparison circuit 121 functions as a comparison means for comparing an image signal for the inspection area detected by the detection unit 400 with an image signal of a corresponding pixel for a reference area so as to detect a difference between the image signals. The delay circuit delays the image signal received from the A/D converter 110 so as to output the image signal for the inspection area that is immediately before the inspection area that is currently being irradiated with inspection light by the scan illustrated in FIG. 11 and that has already been irradiated with inspection light. The difference detection circuit receives the image signal for the inspection area that is currently being irradiated with inspection light from the A/D converter 110 and the image signal from the delay circuit, and detects and outputs a difference between the image signals. Thus, the image comparison circuit 121 compares the image signals for the inspection area and a reference area adjacent thereto. When a defect is present on the inspection area surface, the scattered light scattered by the defect appears as an image signal difference between the adjacent chips.

Instead of the delay circuit, the image comparison circuit 121 may be provided with a memory storing data of an image signal for a conforming chip prepared in advance, so that comparison with the image signal for the inspection area of the conforming item can be made.

The threshold value computing circuit 122 functions as a threshold value computing means for computing a threshold value for comparison with the image signal difference for a pixel corresponding to each inspection area on the basis of a statistic value of the image signal for the pixel, for example. Specifically, the threshold value computing circuit 122 relates the image signal for the inspection area from the A/D converter 110 to the image signal for the respective reference area from the delay circuit on a pixel by pixel basis, calculates the amount of variation (standard deviation) between the inspection areas, and calculates threshold value data used for determining the presence or absence of a defect on the basis of the amount of variation.

The threshold value storing circuit 123 stores the threshold value received from the threshold value computing circuit 122 in association with the coordinate information for the inspection area that is received from the coordinate managing apparatus 140.

The defect determination apparatus 130 is provided with a determination circuit 131 and coefficient tables 132 and 133.

The coefficient tables 132 and 133 store coefficients for changing the threshold value computed by the threshold value computing circuit 122, in association with the wafer coordinate information. The coefficient tables 132 and 133 receive the coordinate information from the coordinate managing apparatus 140 and outputs a coefficient corresponding to the coordinate information to the determination circuit 131. The coefficients stored in the coefficient tables 132 and 133 are multiplied with the threshold value for the corresponding coordinates when outputted to the determination circuit 131. Thus, when a number of the same product is inspected, for example, the threshold value can be flexibly adjusted between a defect-prone location in the inspection area or on the wafer (such as near an edge) and other locations on the basis of the past accumulated inspection/analysis data.

The determination circuit 131 receives the difference signal of the image signals for the corresponding pixel between the inspection area and the reference area from the image comparison circuit 121, the threshold value data for the corresponding pixel that are read from the threshold value storing circuit 123, and the coefficient for changing the threshold value for the corresponding pixel from the coefficient tables 132 and 133.

The determination circuit 131 generates a determination threshold value by multiplying the threshold value from the image processing apparatus 120 with the coefficient for the corresponding pixel from the coefficient table 132 and 133. The determination circuit 131 then determines the presence or absence of a defect by comparing the difference signal from the image comparison circuit 121 with the determination threshold value for the corresponding pixel. At this point, the determination circuit 131 determines that the pixel is due to the scattered light from a defect when the difference signal is not less than the determination threshold value, and outputs the inspection result to the inspection result storage apparatus 150. The determination circuit 131 also outputs the threshold value information used for the determination to the inspection result storage apparatus 150.

The coordinate managing apparatus 140 detects the X-coordinate and the Y-coordinate of the position on the wafer 1 that is currently being irradiated with the inspection light on the basis of the wafer stage position information of the wafer 1 (i.e., position information of the wafer 1) received from the X-scale 30 and the Y-scale 40, and outputs the coordinate information to the image processing apparatus 120, the defect determination apparatus 130, and the inspection result storage apparatus 150. The coordinate managing apparatus 140 stores the arrangement information of the individual inspection areas on the wafer 1. The arrangement information of the individual inspection areas stored in the coordinate managing apparatus 140 is outputted to the image processing apparatus 120 and the coefficient table 132 and 133 as described above.

The inspection result storage apparatus 150 stores the inspection result received from the defect determination apparatus 130 in association with the coordinate information of the corresponding pixel received from the coordinate managing apparatus 140. The inspection result storage apparatus 150 also stores the threshold value information received from the defect determination apparatus 130 in association with the inspection result or coordinate information for the corresponding pixel.

The inspection result may be provided with a function for correcting the variation in the focal point of the detection unit as a result of changes in the atmospheric pressure or atmospheric temperature in the apparatus.

The inspection result display apparatus 160 displays the inspection result information received from the inspection result storage apparatus 150. The inspection result display apparatus 160 also displays a defect candidate image for reviewing a defect candidate. The inspection result display apparatus 160 is an example of a display unit. According to the present embodiment, the illumination unit 300 and the detection unit 400 are a combination of a plurality of illumination means and detection means including the objective lens **20*a*, the spatial filter 21*a*, the image-forming lens 22*a*, and the detector 50*a*, which are dedicated for the illumination means 10*a*, and the objective lens 20*b*, the spatial filter 21*b*, the image-forming lens 22*b*, and the detector 50*b*, which are dedicated for the illumination means 10*b*. Namely, the illumination unit 300 and the detection unit 400 include a plurality of illumination means and detection means. In this case, the inspection result display apparatus 160** may display individual detection results or a result composed from a plurality of detection results.

The input apparatus 170 selects a defect candidate from a map displayed on the inspection result display apparatus 160 when reviewing an inspection result. Alternatively, the input apparatus 170 may input a defect candidate number, or a determination result as to whether the defect candidate is a defect or a false defect. The input apparatus 170 is an example of an input unit.

The result processing apparatus 180 deletes a group of false defects from a group of defect candidates on the basis of the determination result from the input apparatus 170 as to whether the defect candidate is a defect or a false defect, for example. The result processing apparatus 180 also computes a threshold value for not detecting a group of false defects. The result processing apparatus 180 is an example of a processing unit.

The external calculation apparatus 200 reviews a defect candidate on the basis of the inspection result from the inspection result storage apparatus 150 off-line, for example, and generates inspection condition data.

(Inspection Operation)

Next, an outline of an inspection operation by the inspection system according to the present embodiment will be described on the assumption that the automatic setting of the spatial filters **21*a* and 21*b*** has already been completed.

Figure 12:
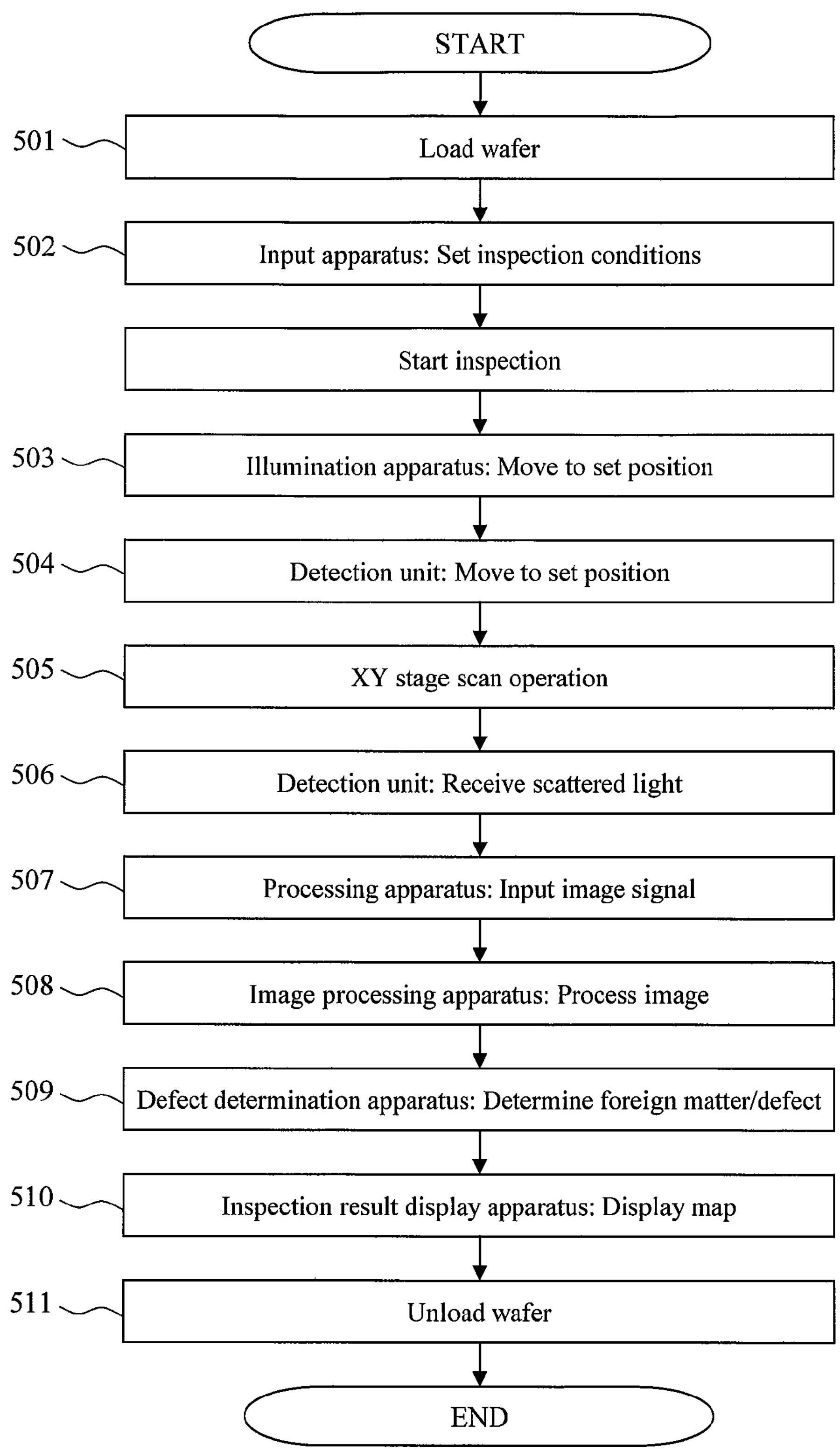
FIG. 12 is a flowchart illustrating an inspection procedure of the inspection system according to an embodiment.

FIG. 12 is a flowchart of the inspection operation performed by the inspection system according to the present embodiment.

In step 501, a wafer is loaded onto the XY stage in the inspection system.

In step 502, inspection condition data, such as the operation speeds of the illumination unit 300, the detection unit 400, and the XY stage, are set from the input apparatus 170. Thereafter, inspection of the wafer is started.

In step 503 immediately after the start of inspection, the illumination unit 300 is moved to a position set by the inspection conditions.

In step 504 immediately thereafter, the detection unit 400 is moved to a position set by the inspection conditions. When a defect and the like in the cell portions is the object of inspection, the arrangement of the spatial filters 21*a* and 21*b* is controlled suitably for the inspection of the cell portions. When a defect and the like in the sense amplifier portions is the object of inspection, the arrangement of the spatial filters 21*a* and 21*b* is controlled suitably for the inspection of the sense amplifier portions.

After these movements are completed, the illumination means 10*a* (10*b*) irradiates inspection light onto the surface of the wafer 1. Simultaneously, an XY stage scan operation is started in step 505. Thus, the entire surface of the wafer 1 is scanned with the inspection light.

In step 506, reflected or scattered light produced by the scattering of the inspection light irradiating the surface of the wafer 1 by a pattern or a defect on the surface of the wafer 1 is received by the detector 50*a* (50*b*) of the detection unit 400.

In step 507, the detector 50*a* (50*b*) converts the intensity of the reflected or scattered light into an electric signal and outputs the electric signal to the processing apparatus 100 as an image signal.

In step 508, an image process is performed by the image processing apparatus 120 of the processing apparatus 100.

In step 509, reflected light or scattered light determined to be a group of defect candidates from the data image-processed in the defect determination apparatus 130 is outputted to the inspection result storage apparatus 150 as an inspection result.

In step 510, the inspection result determined to be the group of defect candidates is displayed on the inspection result display apparatus 160.

In step 511, the wafer is unloaded and the process ends. As described above, in the case of the inspection apparatus according to the present embodiment, only the reflected or scattered light from the cell portions or the sense amplifier portions is selectively blocked with the spatial filters 21*a* and 21*b* optimally arranged, so that only the diffracted or scattered light due to a defect and the like can be imaged. Thus, detection accuracy can be improved over an apparatus according to related art.

Fifth Embodiment

Figure 13:
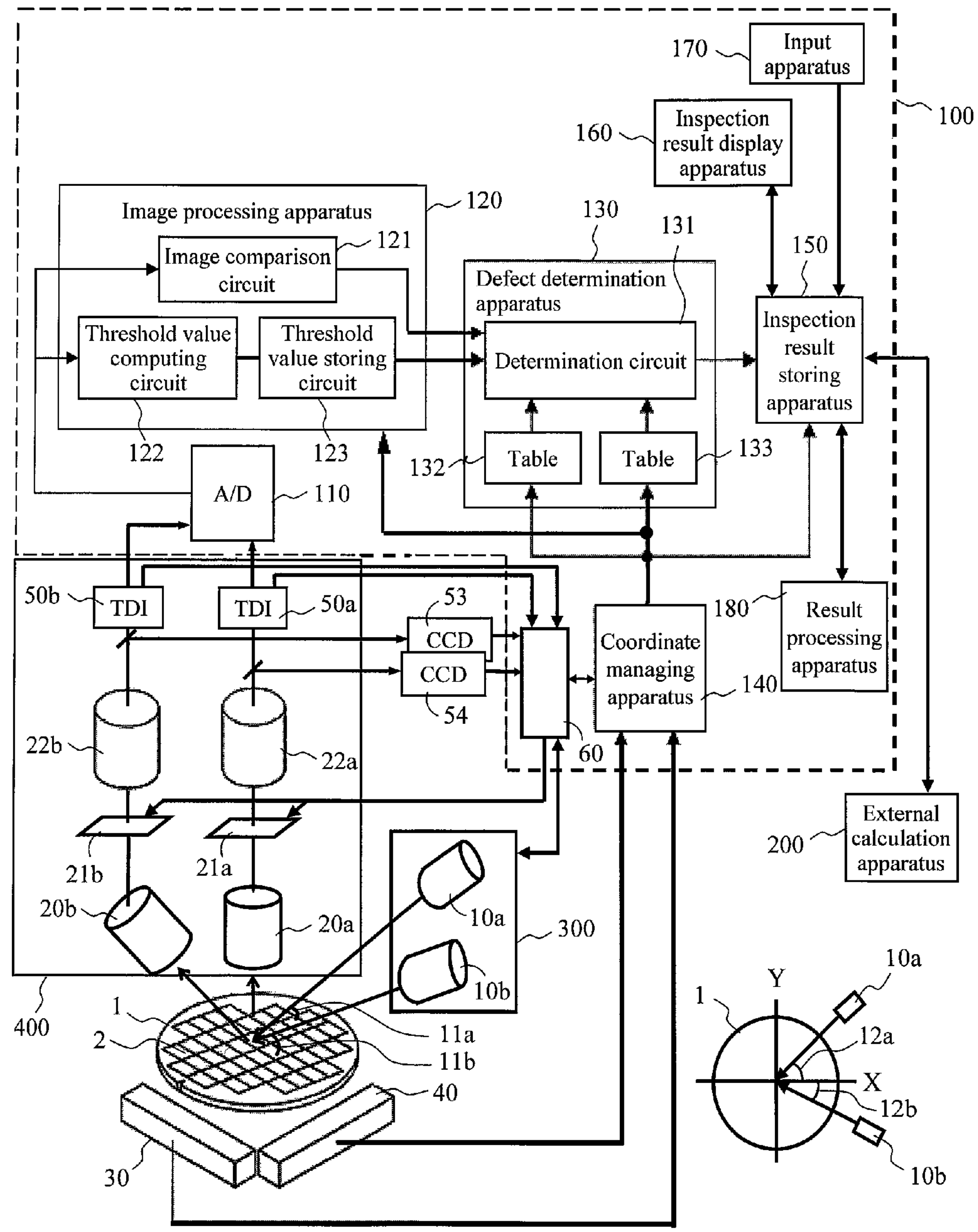
FIG. 13 schematically illustrates another configuration of the inspection system according to an embodiment.

FIG. 13 illustrates another configuration of the inspection system. In FIG. 13, portions corresponding to the portions illustrated in FIG. 10 are designated with similar signs. The present embodiment differs from the fourth embodiment in that the detectors (TDI) 50*a* and 50*b* are used also for acquiring the beam image when determining the setting conditions for the spatial filters 21*a* and 21*b*. Thus, in FIG. 13, signal lines for supplying the beam image (image data) from the detectors (TDI) 50*a* and 50*b* to the spatial filter setting unit 60 are drawn.

According to the present embodiment, the optical system for splitting and guiding the detection light that has passed through the image-forming lenses 22*a* and 22*b* to the respective imaging elements can be simplified. Namely, the present embodiment only requires that half mirrors be disposed on the image forming plane of the image-forming lenses 22*a* and 22*b*. The light flux that has passed through the half mirrors becomes incident on the detectors (TDI) 50*a* and 50*b*, as in the case of FIG. 10, and is imaged as the beam image. Meanwhile, the light flux that has been reflected by the half mirrors becomes directly incident on the detectors (CCD) 53 and 54 and is imaged as the Fourier image.

Thus, according to the present embodiment, the spatial filter setting apparatus 60 receives the image data of the beam image from the detectors 50*a* and 50*b* and the image data of the Fourier image from the detectors 53 and 54.

As described above, according to the present embodiment, the beam image is detected by using the detectors 50*a* and 50*b* that are used for actual inspection. Thus, a state change in intensity profile can be monitored on the basis of the beam image that is acquired under the same conditions as during inspection, and the result can be reflected in the setting of the light-blocking pattern for the spatial filters.

(Summary)

The mode of carrying out the present invention is not limited to the foregoing embodiments, and various modifications may be made within the technical scope of the present invention.

In the following, the main portions of the content disclosed in the present specification will be listed.

(1) An inspection system includes an irradiation unit (300) that irradiates inspection light onto an item to be inspected; a scattered light observation unit (51) that observes an image (beam image) of scattered light produced at or near a surface of the item to be inspected; a diffracted light observation unit (52) that observes an image of diffracted light (Fourier image) which is the Fourier transform of the scattered light produced at or near the surface of the item to be inspected; a spatial filter unit (21*a*, 21*b*) that blocks some of the diffracted light; a detection unit (400) that detects the intensity and position of the scattered light produced at or near the surface of the item to be inspected; a stage unit (70) that can be moved at a variable speed with the item to be inspected mounted thereon; a processing unit (100) that processes information detected by the detection unit; a display unit (160) that displays the information processed by the processing unit; and a spatial filter setting unit (60) that observes an intensity profile of the scattered light image (beam image) and an intensity profile of the diffracted light image (Fourier image) simultaneously, and that determines a setting condition for a spatial filter for selectively blocking the diffracted light due to a specific pattern on the surface of the item to be inspected on the basis of the result of observation.

(2) In the inspection system according to (1), the spatial filter setting unit (60) scans a diffracted light observation field of view with a single spatial filter unit (21*a*, 21*b*), and monitors a state change with respect to the intensity profile of the scattered light image (beam image) and the intensity profile of the diffracted light image (Fourier image) in the absence of insertion of the spatial filter unit simultaneously.

(3) In the inspection system according to (2), the spatial filter setting unit (60) stores a position of the state change in the intensity profile of the scattered light image (beam image) and a position of the state change in the intensity profile of the diffracted light image (Fourier image), and determines the setting condition for the spatial filter unit on the basis of a combination of the two state changes.

(4) In the inspection system according to (3), the spatial filter setting unit (60) determines the number, width, interval, and arrangement of the spatial filter unit as the setting condition.

(5) In the inspection system according to (1), the spatial filter setting unit (60) causes a display unit to display the scattered light image (beam image), the diffracted light image (Fourier image), the intensity profile of the scattered light image, and the intensity profile of the diffracted light image simultaneously.

INDUSTRIAL APPLICABILITY

The present invention may be applied not only to a semiconductor wafer inspection system but also for inspecting a wide variety of objects to be inspected, such as a liquid crystal substrate, a hard disk, and a photomask substrate, for surface scratches, defect, dirt and the like.

DESCRIPTION OF REFERENCE SIGNS

1 Wafer
2 Chip
10*a*, 10*b* Illumination light source
11*a*, 11*b* Elevation angle
12*a*, 12*b* Directional angle of illumination in XY plane
20*a*, 20*b* Objective lens
21*a*, 21*b* Spatial filter
22*a*, 22*b* Image-forming lens
30 X-scale
40 Y-scale
50*a*, 50*b* Detector
51 Detector (beam image)
52 Detector (Fourier image)
53 Detector (Fourier image)
54 Detector (Fourier image)
60 Spatial filter setting apparatus
70 XY stage
100 Processing apparatus
110 A/D converter
120 Image processing apparatus
121 Image comparison circuit
122 Threshold value computing circuit
123 Threshold value storing circuit
130 Defect determination apparatus
131 Determination circuit
132 and 133 Coefficient table
140 Coordinate managing apparatus
150 Inspection result storage apparatus
160 Inspection result display apparatus
170 Input apparatus
180 Result processing apparatus
200 External calculation apparatus
300 Illumination unit
400 Detection unit
800 Image surface of pupil
801A, 801B Slide rail
802 Ultrasonic motor
803 Spatial filter
804 Linear encoder
806 Spatial filter (bar-shaped)
807 Spatial filter (key-shaped)
1000 Irradiation beam
1001 Cell portion
1002 Sense amplifier portion
1003 Fourier image
1004 Diffracted light
1005, 1005*a* to 1005*g* Image of spatial filter in Fourier image
1010 Intensity profile corresponding to sense amplifier portion in beam image
1011 Intensity profile corresponding to cell portion in beam image
1012 Intensity profile of diffracted light in Fourier image
1012*a* Intensity profile eliminated from within Fourier image when diffracted light from sense amplifier portion is blocked
1012*b* Intensity profile eliminated from within Fourier image when diffracted light from cell portion is blocked
1013 Intensity profile in beam image when diffracted light from cell portion is blocked
1014 Intensity profile in beam image when diffracted light of sense amplifier portion is blocked
1020 Beam image
1030 Intensity profile of beam image as a whole
1040 Intensity profile of Fourier image as a whole
1050 Recognition condition (cell portion)
1051 Recognition condition (sense amplifier portion)

The invention claimed is:

1. An inspection system for inspecting a surface of an item to be inspected, the inspection apparatus comprising:

an irradiation unit that irradiates inspection light onto the item to be inspected;

a scattered light observation unit that observes an image of scattered light produced at or near the surface of the item to be inspected;

a diffracted light observation unit that observes an image of diffracted light as the Fourier transform of the scattered light produced at or near the surface of the item to be inspected;

a spatial filter unit that blocks some of the diffracted light;

a detection unit that detects the intensity and position of the scattered light produced at or near the surface of the item to be inspected;

a stage unit that can be moved at a variable speed with the item to be inspected mounted thereon;

a processing unit that processes information detected by the detection unit;

a display unit that displays the information processed by the processing unit;

a spatial filter setting unit that observes an intensity profile of the scattered light image and an intensity profile of the diffracted light image simultaneously, and determines a setting condition for a spatial filter for selectively blocking the diffracted light due to a specific pattern on the surface of the item to be inspected on the basis of an observation result; and wherein the spatial filter setting unit scans a diffracted light observation field of view with a single spatial filter unit, and monitors a state change with respect to the intensity profile of the scattered light image and the intensity profile of the diffracted light image in the absence of insertion of the spatial filter unit simultaneously.

2. The inspection system according to claim 1, wherein the spatial filter setting unit stores a position of the state change in the intensity profile of the scattered light image and a position at which the state change in the intensity profile of the diffracted light image is detected, and determines the setting condition for the spatial filter on the basis of a combination of the two state changes.

3. The inspection system according to claim 2, wherein the spatial filter setting unit determines the number, width, interval, and arrangement of the spatial filter unit as the setting condition.

4. A method of inspecting a surface of an item to be inspected by using an inspection system, the method comprising the steps of:

the inspection system irradiating inspection light onto the item to be inspected;

the inspection system observing an image of scattered light produced at or near the surface of the item to be inspected;

the inspection system observing an image of diffracted light as the Fourier transform of the scattered light produced at or near the surface of the item to be inspected;

the inspection system observing an intensity profile of the scattered light image and an intensity profile of the diffracted light image simultaneously, and determining a setting condition for a spatial filter for selectively blocking the diffracted light due to a specific pattern on the surface of the item to be inspected on the basis of an observation result; and the inspection system scanning a diffracted light observation field of view with a single spatial unit, and monitoring a state change with respect to the intensity profile of the scattered light image and the intensity profile of the diffracted light image in the absence of insertion of the spatial filter unit simultaneously.

5. The inspection method according to claim 4, further comprising a step of storing a position of the state change in the intensity profile of the scattered light image and a position at which the state change in the intensity profile of the diffracted light image is detected, and determining the setting condition for the spatial filter unit on the basis of a combination of the two state changes.

6. The inspection method according to claim 5, further comprising a step of determining the number, width, interval, and arrangement of the spatial filter unit as the setting condition.

* * * * *